United States Patent
Bok et al.

(10) Patent No.: US 6,221,357 B1
(45) Date of Patent: Apr. 24, 2001

(54) FLAVONOIDS DERIVED FROM CITRUS PEELS AS COLLAGEN-INDUCED PLATELET AGGREGATION INHIBITOR

(75) Inventors: Song-Hae Bok; Tae-Sook Jeong, both of Daejeon; Han-Ik Cho; Dong-Soon Lee, both of Seoul, all of (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 09/389,860

(22) Filed: Sep. 2, 1999

(51) Int. Cl.[7] .......................... A61K 35/78; A61K 31/70; A01N 43/04
(52) U.S. Cl. .......................... 424/195.1; 514/27; 514/32; 514/456; 536/8
(58) Field of Search .......................... 424/195.1; 514/27, 514/32, 456; 536/8

(56) References Cited

U.S. PATENT DOCUMENTS 3,867,541 * 2/1975 Robbins ................................ 514/456
4,842,859 * 6/1989 Liu ..................................... 424/195.1
5,762,936 * 6/1998 Ronzio et al. ..................... 424/195.1
5,972,985 * 10/1999 Thomas et al. ....................... 514/400

OTHER PUBLICATIONS

McGregor et al. Thrombosis Research. vol. 94, pp. 235–240, Apr. 1999.*

Beretz et al. Agents and Actions. vol. 12 (3), pp. 382–387, 1982.*

Benavente–Garcia et al. J. Agricult. Food Chem. vol. 45 (12), pp. 4505–4515, 1997.*

Landolfi et al. Biochem. Pharmacol. vol. 33 (9), pp. 1525–1530, abstract enclosed, 1984.*

Zaragoza, et al., "New Inhibitors of Platelet Aggregation In Vivo. Citrus Flavanoids and Hesperidin", An.R. Acad. Farm. (1986), 52(3), pp 497–504.

* cited by examiner

Primary Examiner—Christopher R. Tate
(74) Attorney, Agent, or Firm—Anderson, Kill & Olick, PC

(57) ABSTRACT

A method for inhibiting a collagen-induced platelet aggregation in a mammal comprises administering an effective amount of a flavonoid derived from citrus peels thereto.

5 Claims, No Drawings

FLAVONOIDS DERIVED FROM CITRUS PEELS AS COLLAGEN-INDUCED PLATELET AGGREGATION INHIBITOR

FIELD OF THE INVENTION

The present invention relates to a method for inhibiting a collagen-induced platelet aggregation in a mammal, which comprises administering an effective amount of a flavonoid derived from citrus peels thereto. The flavonoids can be administered to the mammal in the form of a pharmaceutical composition or a food composition.

BACKGROUND OF THE INVENTION

Platelet aggregation on a blood vessel is induced by several factors, e.g., collagen, adenosine diphosphate (ADP), thrombin, epinephrine, ristocetin and arachidonic acid. For instance, when epithelial cells of a blood vessel are damaged, collagen underneath the epithelial cells is exposed to blood stream and activates platelets. The activation of platelets triggers a cascade of reactions resulting in a thrombogenesis and platelet aggregation on the blood vessel, which may cause serious circulatory diseases, e.g., thrombosis, atherosclerosis, cerebral stroke and coronary artery thromboembolism.

Hitherto, various drugs, e.g., thromboxane A2 inhibitor, PGG/H synthase inhibitor, thromoxane synthase inhibitor, thromboxane A2 receptor antagonist, ticlopidine, GP IIb-IIIa inhibitor and serotonin antagonist, have been developed in order to prevent such platelet aggregation. However, these drugs have shown various undesirable side effects on the internal organs, and hemorrhagenic properties.

Ticlopidine and analogues thereof, e.g., clopidogrel, selectively inhibit the ADP-induced platelet aggregation in vivo and are known to be effective in the treatment of a transient ischemic cerebral stroke and peripheral arterial or ischemic heart disease(Hass, W. K. et al., *N. Engl. J. Med.*, 21, 501(1989); and Easton, J. D., *Drugs*, 42, 39(1991)). However, these drugs have been reported to have such undesirable side effects as myelosuppression, increase of total cholesterol level, diarrhea, eruption and neutropenia ((McTavish, E. et al., 2*Drugs*, 40, 238(1990)); Hass, W. K. et al., supra; and Dunn C. D. R., Scrip. Reports, *Stroke: Trends, Treatments and Markets*, PJB Publications Ltd. pp133–139(1995)).

Accordingly, there has continued to exist a need to develop a platelet aggregation inhibitor having a highly selective inhibitory activity on the collagen-induced platelet aggregation and yet without incurring adverse side effects.

It is known that the flavonoids extracted from citrus peel, e.g., naringin, naringenin, hesperidin and hesperetin, have activities in improving lipid metabolism to prevent cardiocirculatory diseases, as well as anticancer and antiviral activities. In particular, it has been reported that both hesperidin and hesperetin have capillary-enhancing, permeability-reducing, anti-inflammation, anti-viral, and blood pressure- and cholesterol-lowering activities(Meyer, O. C., *Angiology*, 45, 579–584(1994); Struckmann, J. R. et al., *Angiol.*, 45, 419–428(1994); Matsubara, Y. et al., *Japan Organic Synthesis Chem. Association Journal*, 52, 318–327 (1994. March); Galati, E. M. et al., *Farmaco.*, 51(3), 219–221(1996, March); Monforte, M. T. et al., *Farmaco.*, 50(9), 595–599(1995, September); JP 95-86929; JP 95-86930; Galati, E. M. et al., *Farmaco.*, 40(11), 709–712 (1994, November); and Emim, J. A. et al., *J. Pharm. Pharmacol.*, 46(2), 118–122(1994)). Further, it has been reported that both naringin and naringenin have anti-cancer, anti-ulcer, and cholesterol-lowering activities(Monforte, M. T. et al., *Farmaco.*, 50(9), 595–599(1995, September); JP 95-86929; JP 95-86930; Felicia, V. et al., *Nutr. Cancer*, 26, 167–181(1996); EP 0352147 A2(1990.1.24); and Martin, M. J. et al., *Parmacol.*, 49, 144–150(1994)).

Recently, it has also been reported that naringenin inhibits an arachidonic acid-induced platelet aggregation(Corcazier, E. et al., *Biochimica Biophysica Acta*, 835, 315–321(1985)).

However, there has been no report on the selective inhibitory activity of flavonoids derived from citrus peels on a collagen-induced platelet aggregation.

SUMMARY OF THE INVENTION

Accordingly, it is a primary object of the present invention to provide a method for inhibiting a collagen-induced platelet aggregation.

In accordance with the present invention, there is provided a method for inhibiting a collagen-induced platelet aggregation in a mammal which comprises administering a flavonoid derived from citrus peels thereto.

DETAILED DESCRIPTION OF THE INVENTION

In accordance with the present invention, flavonoids derived from citrus peels can be administered to a mammal in the form of a pharmaceutical composition or a food composition.

The citrus may be a tangerine, orange, lemon, grapefruit or *Poncirus trifoliata*.

The flavonoids obtainable from citrus peels include naringin, naringenin, hesperidin and hesperetin. These flavonoids may also be synthesized according to the processes described by Zemplen, Bognar, *Ber.*, 75, 1043(1943) and Seka, Prosche, *Monatsh.*, 69, 284(1936). Further, naringenin and hesperetin can be prepared by the hydrolysis of naringin and hesperidin, respectively.

The flavonoids exert a selective inhibitory effect on a collagen-induced platelet aggregation as well as thrombogenesis.

Moreover, in spite of their potent efficacy, the flavonoids show little toxicity or mitogenicity in animal tests. More specifically, the flavonoids exhibit no toxicity when they are orally administered to a mouse at a dosage of 1,000 mg/kg, which corresponds to an oral administration dose of 3 to 10 g per kg of body weight. Further, the flavonoids exert no adverse effects on the liver function.

The present invention also provides a pharmaceutical composition for inhibiting a collagen-induced platelet aggregation, which comprises an effective amount of a flavonoid derived from citrus peels as an active ingredient together with pharmaceutically acceptable excipients, carriers or diluents.

The pharmaceutical formulation may be prepared by using any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulation may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. In case of human, a typical daily dose of flavonoid may range from about 0.5 to 100 mg/kg body weight, preferably 2 to 10 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, the flavonoid can be incorporated in foods, as an additive or dietary supplement, for the purpose of inhibiting the collagen-induced platelet aggregation. Accordingly, the present invention also provide a food composition for inhibiting the collagen-induced platelet aggregation, which comprises an effective amount of the flavonoid. The foods may include meats; chocolates; snacks; confectionery; pizza; foods made from cereal flour such as breads, cakes, crackers, cookies, biscuits, noodles and the likes; gums; dairy products such as milk, cheese, yogurt and ice creams; soups; broths; pastes, ketchups and sauces; vitamin complex; and various health foods. In this case, the content of the flavonoid in a food may range from 0.1 to 50% by weight.

As described above, the flavonoid can be used as an effective, non-toxic pharmaceutical agent for inhibiting the collagen-induced platelet aggregation.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Activity of Flavonoid in Platelet Aggregation Inhibition

Inhibitory activity of the citrus peel flavonoids on the platelet aggregation was determined as follows, in accordance with the methods of O'Brein(O'Brein JR., *J. Clin. Pathol.*, 15, 452(1962)) and Aok(Aok, H. et al., *anesthesiology*, 88, 362(1998)).

9 ml of human blood was added to 1 ml of 3.8 % sodium citrate and the mixture was centrifuged at 1,000 rpm for 10 min. The supernatant(plasma) was diluted with phosphate buffered saline to a concentration of 200,000 to 400,000 platelets/mm$^3$. Each 450 ul of the diluted plasma was put in the cuvettes and 5 ul of a flavonoid solution, wherein naringin, naringenin, hesperidin or hesperetin is dissolved in dimethylsulfoxide at a concentration of 10 mg/L, was added thereto, except for one control cuvette. The mixture was warmed at 37° C. for 3 min. in a platelet aggrometer(Platelet aggrecoder II, PA-3220, Chronolog, U.S.A.). Then, 50 ul of aggregation enhancer solution, i.e., 2 mg/ml collagen solution, 100 uM ADP, 200 uM epinephrine or 15 mg/ml ristocetin, was added thereto. The resulting mixture was reacted at 37° C. for 3 min. and then the optical density thereof was determined. To determine the base line, platelet-free plasma was used.

Consequently, all of naringin, naringenin, hesperidin and hesperetin exhibited an inhibitory activity on the collagen-induced platelet aggregation while they do not inhibit any of ADP-, epinephrine- and ristocetin-induced platelet aggregation. Naringin, naringenin, hesperidin and hesperetin inhibited the collagen-induced platelet aggregation by 59 to 85%, 30 to 87%, 59 to 93%, and 15 to 93%, respectively. The result shows that the flavonoid derived from citrus peels selectively inhibit the collagen-induced platelet aggregation.

EXAMPLE 2

Toxicity of Orally Administered Flavonoid Derived from Citrus Peels 7 to 8 week-old, specific pathogen-free ICR female mice(8 heads) each weighing about 25 to 29 g and male mice(8 heads) each weighing about 34 to 38 g were bred under the condition of temperature 22±1° C., moisture 55±5% and photoperiod 12L/12D. Fodder(Cheiljedang Co., mouse and rat fodder) and water were sterilized and fed to the mice.

A flavonoid derived from citrus peel, naringin or hesperidin, was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of the flavonoid derived from citrus peels. Further, on the 10th day, the mice were sacrificed and the internal organs were visually examined.

All the mice were alive at day 10 and, the flavonoid derived from citrus peels showed no toxicity at a dose of 1,000 mg/kg. The autopsy revealed that the mice did not develop any pathological abnormality, and no weight loss was observed during the 10 day test period. Conclusively, the flavonoid derived citrus peels is not toxic when orally administered to an animal.

EXAMPLE 3

Pharmaceutical Formulation Containing Flavonoid Derived from Citrus Peels

Hard gelatin capsules were prepared using the following ingredients:

|  | Quantity (mg/capsule) |
| --- | --- |
| Active ingredient (Naringin, naringenin, hesperidin, or hesperetin) | 200 |
| Vitamin C | 100 |
| Starch, dried | 180 |
| Magnesium stearate | 20 |
| Total | 500 mg |

EXAMPLE 4

Foods Containing Flavonoid Derived from Citrus Peels

Foods containing a flavonoid derived from citrus peels were prepared as follows.

(1) Preparation of tomato ketchup and sauce

Naringin, naringenin, hesperidin or hesperetin was added to a tomato ketchup or sauce in an amount ranging from 0.01 to 5 wt % to obtain a health-improving tomato ketchup or sauce.

(2) Preparation of wheat flour foods

Naringin, naringenin, hesperidin or hesperetin was added to a wheat flour in an amount ranging from 0.01 to 5 wt % and breads, cakes, cookies, crackers and noodles were prepared by using the mixture to obtain health-improving foods.

(3) Preparation of soups and gravies

Naringin, naringenin, hesperidin or hesperetin was added to soups and gravies in an amount ranging from 0.01 to 5 wt % to obtain health-improving soups and gravies.

(4) Preparation of ground beef

Naringin, naringenin, hesperidin or hesperetin was added to ground beef in an amount ranging from 0.01 to 5 wt % to obtain a health-improving ground beef.

(5) Preparation of dairy product

Naringin, naringenin, hesperidin or hesperetin was added to milk in an amount ranging from 0.01 to 5 wt % and various dairy products such as butter and ice cream were prepared by using the milk.

However, in case of cheese preparation, naringin, naringenin, hesperidin or hesperetin was added to the coagulated milk protein; and, in case of yogurt preparation, naringin, naringenin, hesperidin or hesperetin was added to the coagulated milk protein obtained after the fermentation.

While the invention has been described with respect to the above specific embodiments, it should be recognized that various modifications and changes may be made to the invention by those skilled in the art which also fall within the scope of the invention as defined by the appended claims.

What is claimed is:

1. A method for selectively inhibiting a collagen-induced platelet aggregation in a mammal, which comprises administering an effective amount of a flavonoid selected from the group consisting of naringin, hesperidin, hesperetin and a mixture thereof to a mammal in need of a treatment for said platelet aggregation.

2. The method of claim 1, wherein the mammal is human.

3. The method of claim 1, wherein the flavonoid is administered in the form of a pharmaceutical composition or a food composition.

4. The method of claim 3, wherein the effective amount of the flavonoid contained in the pharmaceutical composition ranges from 0.5 to 100 mg/kg body weight/day.

5. The method of claim 3, wherein the content of the flavonoid in the food composition ranges from 0.1 to 50% by weight.

\* \* \* \* \*